United States Patent

(12) United States Patent
Tromp

(10) Patent No.: US 10,408,651 B2
(45) Date of Patent: Sep. 10, 2019

(54) METHOD FOR DETERMINING A PULSE DURATION $T_{90}$ OF A 90° PULSE IN A NUCLEAR MAGNETIC MEASURING METHOD AND RESPECTIVE NUCLEAR MAGNETIC FLOWMETER

(71) Applicant: Krohne AG, Basel (CH)

(72) Inventor: Rutger Reinout Tromp, Dordrecht (NL)

(73) Assignee: KROHNE AG, Basel (CH)

( * ) Notice: Subject to any disclaimer, the term of this patent is extended or adjusted under 35 U.S.C. 154(b) by 170 days.

(21) Appl. No.: 15/439,046

(22) Filed: Feb. 22, 2017

(65) Prior Publication Data

US 2017/0241821 A1  Aug. 24, 2017

(30) Foreign Application Priority Data

Feb. 22, 2016 (DE) .................. 10 2016 103 038

(51) Int. Cl.
*G01R 33/563* (2006.01)
*G01R 33/44* (2006.01)
(Continued)

(52) U.S. Cl.
CPC ............. *G01F 1/716* (2013.01); *G01R 33/36* (2013.01); *G01R 33/3628* (2013.01);
(Continued)

(58) Field of Classification Search
USPC ......................... 324/300–322; 600/407–435; 382/128–131
See application file for complete search history.

(56) References Cited

U.S. PATENT DOCUMENTS 3,135,912 A * 6/1964 Baker ...................... G01V 3/32
324/303
4,633,181 A * 12/1986 Murphy-Boesch ........................
G01R 33/3628
324/318

(Continued)

*Primary Examiner* — Melissa J Koval
*Assistant Examiner* — Tiffany A Fetzner
(74) *Attorney, Agent, or Firm* — David S. Safran; Roberts Mlotkowski Safran Cole & Calderon, P.C.

(57) ABSTRACT

A method for determining a pulse duration $T_{90}$ of a 90° pulse in a nuclear magnetic measuring method. A signal generator has a known generator resistance $R_S$, wherein a coil has a coil impedance $Z_L$ with a coil resistance $R_L$ and a coil reactance $X_L$, wherein a coupling circuit has an adjustable matching capacitance $C_M$ and an adjustable tuning capacitance $C_T$, and wherein the medium has a Larmor precession having an angular Larmor frequency $\omega_P$. The time needed for determining the pulse duration $T_{90}$ of the 90° pulse is reduced by the matching capacitance $C_M$ and the tuning capacitance $C_T$ being set so that the angular resonance frequency $\omega_0$ corresponds to the angular Larmor frequency $\omega_P$ and by power matching being present between the signal generator and the coil. The coil resistance $R_L$ is determined and the pulse duration $T_{90}$ is determined as a function of the coil resistance $R_L$.

14 Claims, 1 Drawing Sheet

(51) Int. Cl.
 *G01R 33/36* (2006.01)
 *G01R 33/30* (2006.01)
 *G01N 24/08* (2006.01)
 *G01F 1/716* (2006.01)

(52) U.S. Cl.
 CPC ....... *G01R 33/44* (2013.01); *G01R 33/56308* (2013.01); *G01N 24/08* (2013.01); *G01R 33/307* (2013.01); *G01R 33/3607* (2013.01)

(56) References Cited

U.S. PATENT DOCUMENTS

| | | | |
|---|---|---|---|
| 8,193,811 B2* | 6/2012 | Tropp | G01R 33/3415 324/318 |
| 2010/0301862 A1* | 12/2010 | Tropp | G01R 33/3415 324/318 |
| 2017/0276752 A1* | 9/2017 | Dai | G01R 33/3607 |

* cited by examiner

10: Signal source
11: Generator resistor
12: Matching capacitor
13: Tuning capacitor

METHOD FOR DETERMINING A PULSE DURATION $T_{90}$ OF A 90° PULSE IN A NUCLEAR MAGNETIC MEASURING METHOD AND RESPECTIVE NUCLEAR MAGNETIC FLOWMETER

BACKGROUND OF THE INVENTION

Field of the Invention

The invention relates to a method for determining a pulse duration $T_{90}$ of a 90° pulse in a nuclear magnetic measuring method with a circuit arrangement. Thereby, the circuit arrangement has a signal generator for generating the 90° pulse, a coil for transmitting the 90° pulse to a medium, a coupling circuit and an angular resonance frequency $\omega_0$. The signal generator has a known generator resistance $R_S$. The coil has a coil impedance $Z_L$ with a coil resistance $R_L$ and a coil reactance $X_L$ according to $Z_L=R_L+jX_L$. The coupling circuit has a matching capacitor having an adjustable matching capacitance $C_M$ and a tuning capacitor having an adjustable tuning capacitance $C_T$. The medium is magnetized by a magnetic field for the nuclear magnetic measuring method and has a Larmor precession having an angular Larmor frequency $\omega_P$.

Description of Related Art

The invention further relates to a nuclear magnetic flowmeter for a nuclear magnetic measuring method having a circuit arrangement and a control unit. Thereby, the circuit arrangement has a signal generator for generating a 90° pulse, a coil for transmitting the 90° pulse to a medium, a coupling circuit and an angular resonance frequency $\omega_0$. The signal generator has a known generator resistance $R_S$. The coil has a coil impedance $Z_L$ with a coil resistance $R_L$ and a coil reactance $X_L$ according to $Z_L=R_L+jX_L$. The coupling circuit has a matching capacitor having an adjustable matching capacitance $C_M$ and a tuning capacitor having an adjustable tuning capacitance $C_T$. The medium is magnetized by a magnetic field for the nuclear magnetic measuring method and has a Larmor precession having an angular Larmor frequency $\omega_P$.

The circuit arrangement has an angular resonance frequency $\omega_0$, since it is designed as a resonant circuit.

A Nuclear magnetic measuring method requires that a medium, for which the nuclear magnetic measurements of the method are to be carried out, contains atomic nuclei that have a nuclear spin and thereby also a magnetic moment. The nuclear spin of an atomic nucleus is understood as an angular momentum describable by a vector and, accordingly, the magnetic moment of the atomic nucleus is described by a vector that is aligned parallel to the vector of the angular momentum. In the presence of a magnetic field, the vector of the magnetic moment of the atomic nucleus tends to be aligned parallel to the vector of the magnetic field at the location of the atomic nucleus. Thereby, the vector of the magnetic moment precesses around the vector of the magnetic field at the location of the atomic nucleus. The precession is known as Larmor precession. The angular frequency of the Larmor precession is called angular Larmor frequency $\omega_P$ and is the product of the gyromagnetic ratio and the absolute value of the magnetic flux density at the location of the atomic nucleus.

Nuclear magnetic measuring methods are based on the magnetization, by means of a magnetic field, of a plurality of atomic nuclei each having a magnetic moment in a volume of a medium. In the absence of a magnetic field, the individual alignment of the vectors of the magnetic moments is statistically uniformly distributed, which is why the medium is not magnetized in the volume. The presence of a magnetic field disturbs the statistically uniform distribution of the individual alignment of the vectors of the magnetic moment, whereby a magnetization parallel to the magnetic field is formed in the medium in the volume. Macroscopic magnetization is understood in general under magnetization. The temporal course of the process of alignment of the individual vectors of the magnetic moments in a magnetic field is characterized by the spin-lattice relaxation time constant and has an exponentially decreasing course. The values of the spin-lattice relaxation time constants are characteristic for different substances, wherein substances can also be called phases.

Nuclear magnetic measuring methods determine, for example, the flow of a medium through a measuring tube of a nuclear magnetic flowmeter or, in a medium having several phases, i.e. at least two phases, the portions of the individual phases in the medium. A combination of nuclear magnetic measuring methods is also possible. For example, a nuclear magnetic measuring method determines the portions of the individual phases of the medium as well as the flow of the individual phases through the measuring tube for a medium having several phases. Both the mass flow and the volume flow of a medium are called flow.

In a medium having several phases, determining the portion of the individual phases in the medium does not only require that each of the phases has atomic nuclei with magnetic moments, so that the phases can be magnetized in a magnetic field, but also that the individual phases of the medium have different spin-lattice relaxation time constants, so that the individual phases can be differentiated from one another. The medium extracted from oil sources, for example, consists essentially of the liquid phases crude oil and saltwater and the gaseous phase natural gas. Thereby, all phases contain hydrogen atom nuclei. Since hydrogen atom nuclei have the greatest gyromagnetic ratio of all atomic nuclei and the individual phases also have different spin-lattice relaxation time constants, nuclear magnetic flowmeters are suitable, in particular, for the measurement of flow of the multi-phase medium extracted from oil sources. Phases having hydrogen atomic nuclei are, in particular, suitable for nuclear magnetic measuring methods, however, phases having atomic nuclei with a smaller gyromagnetic ratio than that of hydrogen atomic nuclei, such as sodium atomic nuclei, are also suitable for nuclear magnetic measuring methods.

Nuclear magnetic measuring methods generally also include nuclear magnetic measurements of the magnetization of a medium in a volume after a certain exposure duration to a magnetic field. Such a nuclear magnetic measurement requires the previous rotation of an angle of 90° of the vectors of the magnetic moments of the atomic nuclei of the magnetized medium in the volume in relation to the vector of the magnetic field. The vectors of the magnetic moments rotated at an angle of 90° cause a measuring signal in a sensor, which represents the magnetization of the medium in the volume. Such a sensor is, for example, a sensor coil, in which the magnetic moments precessing with the angular Larmor frequency $\omega_P$ induce a voltage as measuring signal. The strength of the measuring signal is at a maximum at a rotation of an angle of 90° and becomes less when the rotation of an angle of 90° does not occur.

A rotation of the vectors of the magnetic moments of the atomic nuclei of the magnetized medium in the volume in respect to the vector of the magnetic field is carried out using an electromagnetic pulse, to which the magnetized medium in the volume is exposed. Such a pulse has an angular frequency $\omega_K$ that corresponds to the angular Larmor frequency $\omega_P$ of the medium, whereby a torque acts on the magnetic moments of the atomic nuclei of the medium in the volume, which then causes the rotation. The angle of rotation is specified by the pulse duration of the pulse. The pulse duration is, thereby, to be differentiated from the period duration $T_K = 2\pi/\omega_K$ of an individual electromagnetic oscillation of a pulse. An electromagnetic pulse that causes a rotation of an angle of 90° is called a 90° pulse and the pulse duration is called pulse duration $T_{90}$. The pulse duration $T_{90}$ is, thereby, in particular dependent on the medium. A 90° pulse has exactly one single pulse duration $T_{90}$.

It is known from the prior art to determine the pulse duration $T_{90}$ required for a given medium in that a measuring series of nuclear magnetic measurements of the magnetization at different pulse durations is carried out in a volume of the medium with a constant magnetization. The pulse duration that causes a rotation of the magnetic moments of an angle that comes closest to an angle of 90° is the pulse duration, at which the strongest measuring signal of the measuring series is measured. This pulse duration $T_{90}$ is assigned to the pulse duration to be set for a rotation of an angle of 90°. The prior art has, in particular, the disadvantage of requiring a large amount of time for carrying out the measuring series.

SUMMARY OF THE INVENTION

Thus, the object of the invention is to provide a method for determining a pulse duration $T_{90}$ of a 90° pulse in a nuclear magnetic measuring method and to provide a nuclear magnetic flowmeter for a nuclear magnetic measuring method, in which the time needed for determining the pulse duration $T_{90}$ of the 90° pulse is reduced in comparison to the prior art.

The invention relates to a method for determining a pulse duration $T_{90}$ of a 90° pulse according to a first teaching using a nuclear magnetic measuring method, in which the derived and described object is achieved. The method according to the invention is initially and essentially characterized by the following method steps:

In a first method step, the matching capacitance $C_M$ and the tuning capacitance $C_T$ are set so that the angular resonance frequency $\omega_0$ corresponds to the angular Larmor frequency $\omega_P$ and that power matching is present between the signal generator and the coil. In a second method step, the coil resistance $R_L$ is determined. In a third method step, the pulse duration $T_{90}$ is calculated as a function of the coil resistance $R_L$.

Thereby, the angular resonance frequency $\omega_0$ is specified by the circuit topology of the circuit arrangement, the generator resistance $R_S$, the coil impedance $Z_L$, the matching capacitance $C_M$, and the tuning capacitance $C_T$. The generator resistance $R_S$ generally represents the characteristic impedance of the signal generator, which is usually 50Ω. The coil reactance $X_L$ of the coil impedance $Z_L$ has an inductive component $L_L$ and a capacitive component $C_L$ according to $X_L = \omega_0 L_L - 1/(\omega_0 C_L)$ at the angular resonance frequency $\omega_0$. Power matching effectuates that a maximum of the power given off from the signal generator by the 90° pulse is converted in the coil. Power matching is for example implemented by maximizing the current injected into the coil by the signal generator. The setting of the angular resonance frequency $\omega_0$ to the angular Larmor frequency $\omega_P$ effectuates that the angular frequency of the 90° pulse corresponds to the angular Larmor frequency $\omega_P$ and the 90° pulse exerts a torque on the magnetic moments of the atomic nuclei of the magnetized medium, whereby the vectors of the magnetic moment are rotated by 90° in respect to the vector of the magnetic field.

The coupling circuit has an input and an output, wherein the input is connected to the signal generator and the output is connected to the coil. Usually, the tuning capacitor and the coil are connected in parallel and the signal generator, the matching capacitor, and the parallel circuit consisting of the tuning capacitor and the coil are connected in series.

The coil resistance $R_L$ is determined in that the equations for the circuit arrangement according to Kirchhoff's circuit laws are solved for the coil resistance $R_L$. The equations represent the circuit topology.

In one implementation of the method according to the invention, it is provided that the function is described by the equation $$R_L = A + BT_{90} - CT_{90}^3 + \frac{DT_{90}}{E + T_{90}^2}$$

wherein A, B, C, D and E are stored constants. The pulse duration $T_{90}$ is determined from the equation in that the equation is solved for the pulse duration $T_{90}$. The stored constants A, B, C, D and E, thereby, are real numbers.

The implementation is based on several findings:

First, it has been found that the coil resistance $R_L$ is described by three components, namely $R_r$, $R_i$, and $R_d$, according to $R_L = R_r + R_i + R_d$. The first component $R_r$ represents the ohmic resistance of the electric lines that form the coil. The second component $R_i$ describes the heating in the medium by the 90° pulse due to induction. The third component $R_d$ describes the heating in the medium by the 90° pulse due to dielectric coupling with the medium.

It has been further found that the three components $R_r$, $R_i$, and $R_d$ can be described at the Larmor frequencies that occur in nuclear magnetic measuring methods according to $$R_r + R_i + R_d = A' + B'\sigma - C'\sigma^3 + \frac{D'\sigma}{E' + \sigma^2}$$

so that $$R_L = A' + B'\sigma - C'\sigma^3 + \frac{D'\sigma}{E' + \sigma^2}$$

is valid. Thereby, A', B', C', D' and E' are constants and $\sigma$ is the specific conductance of the medium.

It has been further found that the pulse duration $T_{90}$ is proportional to the specific conductance $\sigma$ of the medium according to $\sigma = KT_{90}$, wherein K is a constant so that $$R_L = A + BT_{90} - CT_{90}^3 + \frac{DT_{90}}{E + T_{90}^2}$$

is valid.

In a further implementation of the method according to the invention, it is provided that the coil resistance $R_L$ is determined using the generator resistance $R_S$, the angular resonance frequency $\omega_0$, the matching capacitance $C_M$ and the tuning capacitance $C_T$.

It has been found that the coil reactance $X_L$ of the coil impedance $Z_L$ changes only little at a plurality of applications. For this reason, in an implementation alternative to the above implementation, the coil reactance $X_L$ is assumed to be a constant and the coil resistance $R_L$ is determined using the generator resistance $R_S$, the angular resonance frequency $\omega_0$ and either the matching capacitance $C_M$ or the tuning capacitance $C_T$. This is possible because the equations for the circuit arrangement according to Kirchhoff's circuit laws are over-determined due to the assumption of a constant coil reactance $X_L$. Thus, either the matching capacitance $C_M$ or the tuning capacitance $C_T$ can be used for determining the coil resistance $R_L$. This implementation offers the advantage of a reduced effort in determining the coil resistance $R_L$.

In a further development of the above implementation, it is provided that the coil reactance $X_L$ assumed as constant is determined using the generator resistance $R_S$, the angular resonance frequency $\omega_0$, the matching capacitance $C_M$ and the tuning capacitance $C_T$. For this determination, the equations for the circuit arrangements according to Kirchhoff's circuit laws are solved for the coil reactance $X_L$. The coil reactance $X_L$ determined in this manner is then used in a method according to the above implementation.

At power matching, a maximum of the power given off by the signal generator is converted in the coil. In order to set power matching, a measure for power matching is necessary. For this reason, it is provided in a further implementation that a measure for power matching is composed, in that the power of the 90° pulse at the signal generator and the power of the 90° pulse reflected at the coil are determined and a ratio between the reflected power of the 90° pulse and the power of the 90° pulse is determined. No power is reflected at the coil at power matching.

In case the determination of the pulse duration $T_{90}$ from the coil resistance $R_L$ is carried out using the constants A, B, C, D and E, it is provided in a further implementation, that the constants A, B, C, D and E are determined from a system of equations, in that the coil resistance $R_L$ is determined for at least five different pulse durations $T_{90}$ of the 90° pulse and the respective determined coil resistance $R_L$ and the respective pulse duration $T_{90}$ are each applied to an equation according to $$R_L = A + BT_{90} - CT_{90}^3 + \frac{DT_{90}}{E + T_{90}^2}.$$

The system of equations has five unknowns, namely the constants A, B, C, D and E, and at least five equations, wherein the coil resistance $R_L$ and the pulse duration $T_{90}$ are known in each of the equations. The determined constants A, B, C, D and E are stored in a further development of the above implementations and used in the method according to the invention.

It has been found that the angular Larmor frequency $\omega_P$ is subject to fluctuations and that the effect of a fluctuation of the angular Larmor frequency $\omega_P$ on both the matching capacitance $C_M$ as well as the tuning capacitance $C_T$ can be compensated by scaling. Thus, it is provided in a further implementation that the matching capacitance $C_M$ and/or the tuning capacitance $C_T$ is/are scaled, in that a quotient of the angular resonance frequency $\omega_0$ as dividend and a reference angular resonance frequency $\omega_0''$ as divisor is formed and the quotient is multiplied by the matching capacitance $C_M$ or, respectively, the tuning capacitance $C_T$. The determination of scaling is carried out, for example, according to the equations $$C_M^n = \left(\frac{\omega_0}{\omega_0^n}\right) C_M \text{ and } C_T^n = \left(\frac{\omega_0}{\omega_0^n}\right) C_T.$$

In the equations, the upper index n identifies the scaled matching capacitance $C_M$ and the scaled tuning capacitance $C_T$. The reference angular resonance frequency $\omega_0''$ is an angular resonance frequency $\omega_0$.

In a further development of the above implementation, it is provided that the magnetic field is generated by permanent magnets and the reference angular resonance frequency $\omega_0''$ is determined at one temperature of the permanent magnets. This implementation is based on the findings that, on the one hand, the angular Larmor frequency $\omega_P$ is, in particular, a function of the absolute value of the magnetic flux density of the magnetic field and that, on the other hand, the magnetic field strength generated by the permanent magnets, and thus also the magnetic flux density in the medium, is a function of the temperature. The effect of fluctuations in temperature of the permanent magnets on the set matching capacitance $C_M$ and/or the set tuning capacitance $C_T$ is compensated in this implementation.

The invention relates to a nuclear magnetic flowmeter for a nuclear magnetic measuring method according to a second teaching, in which the derived and described object is achieved. The nuclear magnetic flowmeter according to the invention is initially and essentially wherein the control unit determines a pulse duration $T_{90}$ of the 90° pulse in nuclear magnetic measuring methods. The determination is carried out in that the control unit sets the matching capacitance $C_M$ and the tuning capacitance $C_T$ so that the angular resonance frequency $\omega_0$ corresponds to the angular Larmor frequency $\omega_P$ and that power matching is present between the signal generator and the coil, in that the control unit determines the coil resistance $R_L$ and in that the control unit determines the pulse duration $T_{90}$ as a function of the coil resistance $R_L$.

The explanations in respect to the method according to the invention are also accordingly valid for the nuclear magnetic flowmeter according to the invention and vice versa.

One implementation of the nuclear magnetic flowmeter according to the invention provides that the control unit is designed to carry out one of the methods according to the invention as described above.

In detail, there is a plurality of possibilities for designing and further developing the method according to the invention and the nuclear magnetic flowmeter according to the invention. Reference is made to the patent claims subordinate to patent claims 1 and 10 as well as to the following description of a preferred embodiment in conjunction with the drawing. The drawing shows

DETAILED DESCRIPTION OF THE INVENTION

Figure 1:
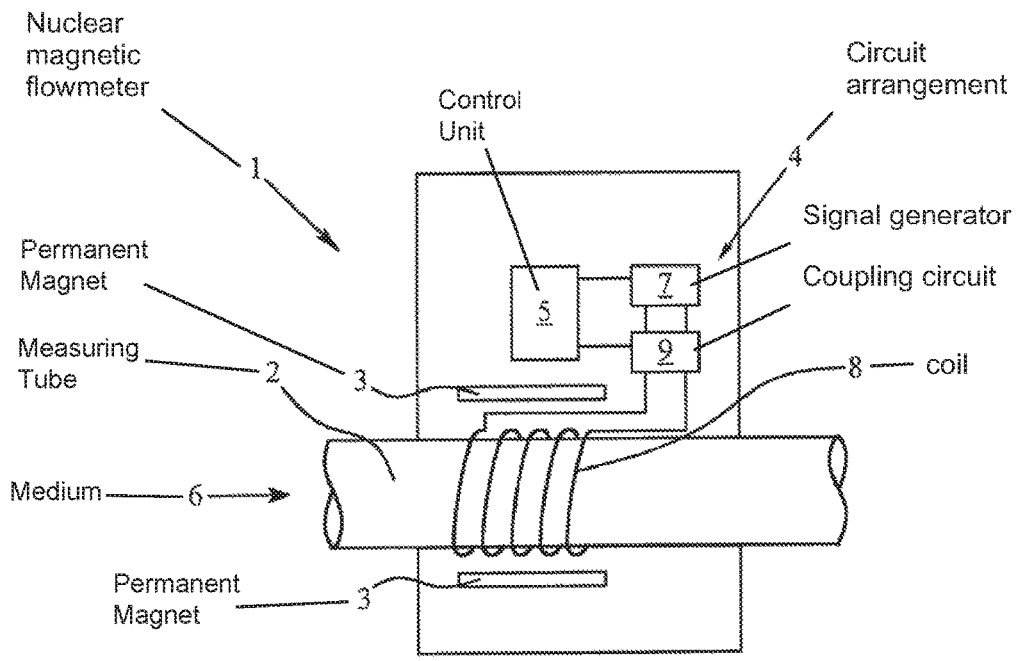
FIG. 1 schematically shows an embodiment of a nuclear magnetic flowmeter.

FIG. 1 shows an embodiment of a nuclear magnetic flowmeter 1 for nuclear magnetic measuring methods in operation. FIG. 1 shows the measuring tube 2, the permanent magnets 3, the circuit arrangement 4 and the control unit 5 of the nuclear magnetic flowmeter 1.

The measuring tube 2 has a medium 6 flowing through it, wherein the medium 6 has several phases. The permanent magnets 3 generate a magnetic field that magnetizes the medium 6 in a volume so that the medium 6 has a Larmor precession with the angular Larmor frequency $\omega_P$. The nuclear magnetic flowmeter 1 is designed to carry out nuclear magnetic measuring methods, which, for example, determine the flow velocity of the phases of the medium 6 through the measuring tube 2 and the portions of the individual phases in the medium 6.

Figure 2:
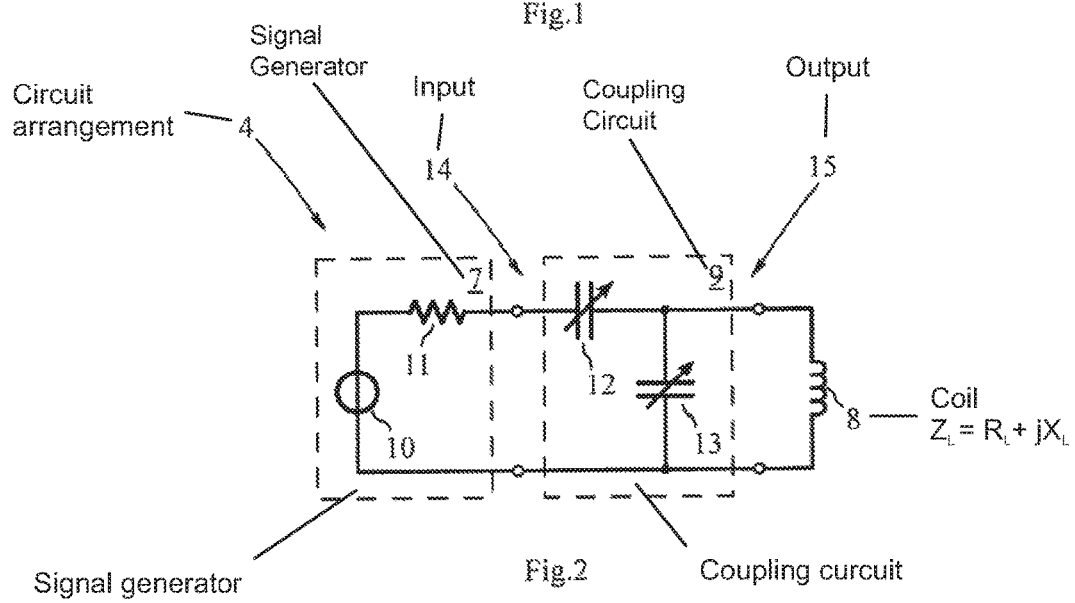
FIG. 2 is a simplified circuit diagram of the circuit arrangement of the nuclear magnetic flowmeter of FIG. 1.

FIG. 2 shows a simplified circuit diagram of the essential elements of the circuit arrangement 4. The circuit arrangement 4 is comprised of the signal generator 7 for generating a 90° pulse, the coil 8 for transmitting the 90° pulse to the medium 6, and the coupling circuit 9.

The signal generator 7 essentially has the signal source 10 and the generator resistor 11, wherein the generator resistor 11 has the chosen and, thus, known generator resistance $R_S$. The generator resistance $R_S$ represents the characteristic impedance of the signal generator 7 and is 50Ω in this embodiment.

The coil 8 has the coil impedance $Z_L$ with the coil resistance $R_L$ and the coil reactance $X_L$ according to $Z_L = R_L + jX_L$.

The coupling circuit 9 in this embodiment consists of the matching capacitor 12 with the adjustable matching capacitance $C_M$ and the tuning capacitor 13 with the tuning capacitance $C_T$ and has the input 14 and the output 15. The input 14 of the coupling circuit 9 is connected to the signal generator 7 and the output 15 of the coupling circuit 9 is connected to the coil 8. Thereby, the tuning capacitor 13 and the coil 8 are connected in parallel and the signal source 10, the generator resistor 11, the matching capacitor 12 and the parallel circuit consisting of the tuning capacitor 13 and the coil 8 are connected in series.

The circuit arrangement 4 is a resonant circuit that has the angular resonance frequency $\omega_0$, wherein the angular resonance frequency $\omega_0$ is determined by the topology of the circuit arrangement 4, the generator resistance $R_S$, the matching capacitance $C_M$, the tuning capacitance $C_T$ and the coil impedance $Z_L$.

The generator resistor 11, the matching capacitor 12, the tuning capacitor 13 and the coil 8 are all devices in the circuit arrangement 5, whereas the generator resistance $R_S$, the matching capacitance $C_M$, the tuning capacitance $C_T$ and the coil impedance $Z_L$ are all properties of the above devices.

The control unit 5 in this embodiment determines a pulse duration $T_{90}$ of a 90° pulse in nuclear magnetic measuring methods using the method with the following method steps:

In a first method step, the matching capacitance $C_M$ of the matching capacitor 12 and the tuning capacitance $C_T$ of the tuning capacitor 13 are set so that the angular resonance frequency $\omega_0$ corresponds to the angular Larmor frequency $\omega_P$ of the magnetized medium 6 and that power matching is present between the signal generator 7 and the coil 8.

In a second method step, the coil resistance $R_L$ is determined in that the equations for the circuit arrangement 4 according to Kirchhoff's circuit laws are solved for the coil resistance $R_L$ and the coil resistance $R_L$ is determined using the generator resistance $R_S$, the angular resonance frequency $\omega_0$, the matching capacitance $C_M$ and the tuning capacitance $C_T$.

In a third method step, the pulse duration $T_{90}$ is determined from a function of the coil resistance $R_L$, which is described by the equation $$R_L = A + BT_{90} - CT_{90}^3 + \frac{DT_{90}}{E + T_{90}^2}$$

In this, A, B, C, D and E are previously stored constants. Determination is carried out in that the equation is solved for the pulse duration $T_{90}$ and the determined coil resistance $R_L$ is used.

In this embodiment of the invention, the matching capacitance $C_M$ and the tuning capacitance $C_T$ are scaled with a reference angular resonance frequency $\omega_0''$ determined at one temperature of the permanent magnets, whereby the impact of a fluctuation of the temperature of the permanent magnets on the matching capacitance $C_M$ and the tuning capacitance $C_T$ is compensated. For scaling, a quotient is first formed from the angular resonance frequency $\omega_0$ as dividend and the reference angular resonance frequency $\omega_0''$ as divisor. The quotient is thus $\omega_0/\omega_0''$. Then, the quotient is multiplied by the matching capacitance $C_M$ or the tuning capacitance $C_T$. Thus, the scaled matching capacitance is $$C_M^n = \left(\frac{\omega_0}{\omega_0^n}\right)C_M$$

and the scaled tuning capacitance is $$C_T^n = \left(\frac{\omega_0}{\omega_0^n}\right)C_T.$$

In the equations, the upper index n indicates the scaled matching capacitance $C_M$ and the scaled tuning capacitance $C_T$.

The stored constants A, B, C, D and E have been determined in that a system of equations was formed using the above-described method. The system of equations was formed in this embodiment in that the coil resistance $R_L$ was determined for ten different pulse durations $T_{90}$ of the 90° pulse and the respective, determined coil resistance $R_L$ and the respective pulse duration $T_{90}$ were each applied to an equation according to $$R_L = A + BT_{90} - CT_{90}^3 + \frac{DT_{90}}{E + T_{90}^2}.$$

The system of equations has five unknowns, namely A, B, C, D and E and has ten equations, wherein the coil resistance $R_L$ and the pulse duration $T_{90}$ are known in each of the ten equations. Consequently, the system of equations is overdetermined and the constants A, B, C, D and E were determined from the system of equations. Due to the overdetermination, the accuracy of the determination of the constants A, B, C, D and E is increased compared to determination with the required at least five equations.

What is claimed is:

1. A method for determining a pulse duration $T_{90}$ of a 90° pulse in a nuclear magnetic measuring method with a circuit arrangement that has a signal generator for generating the 90° pulse that has a known generator resistance $R_S$, a coil for transmitting the 90° pulse to a medium that has a coil impedance $Z_L$ with a coil resistance $R_L$ and a coil reactance $X_L$ according to $Z_L=R_L+jX_L$, a coupling circuit has a matching capacitor having an adjustable matching capacitance $C_M$ and a tuning capacitor (13) having an adjustable tuning capacitance $C_T$, and an angular resonance frequency $\omega_0$, the method comprising:

magnetizing the medium by a magnetic field that has a Larmor precession having an angular Larmor frequency $\omega_P$, setting the matching capacitance $C_M$ and the tuning capacitance $C_T$ of the coupling circuit so that the angular resonance frequency $\omega_0$ corresponds to the angular Larmor frequency $\omega_P$ and power matching is present between the signal generator and the coil in circuit arrangement, determining the coil resistance $R_L$, in circuit arrangement after the setting of the matching and tuning capacitances determining the pulse duration $T_{90}$ of the 90° pulse in the nuclear magnetic measuring method as a function of the coil resistance $R_L$, and outputting the pulse duration determined.

2. The method according to claim 1, wherein the function of the coil resistance $R_L$ is $$R_L = A + BT_{90} - CT_{90}^3 + \frac{DT_{90}}{E + T_{90}^2}$$

wherein A, B, C, D and E are stored constants.

3. The method according to claim 1, wherein the coil resistance $R_L$ is determined by using the generator resistance $R_S$, the angular resonance frequency $\omega_0$, the matching capacitance $C_M$ and the tuning capacitance $C_T$.

4. The method according to claim 1, wherein the coil reactance $X_L$ is assumed to be constant and the coil resistance $R_L$ is determined by using the generator resistance $R_S$, the angular resonance frequency $\omega_0$, and either the matching capacitance $C_M$ or the tuning capacitance $C_T$.

5. The method according to claim 4, wherein the coil reactance $X_L$ that is assumed to be constant is determined by using the generator resistance $R_S$, the angular resonance frequency $\omega_0$, the matching capacitance $C_M$ and the tuning capacitance $C_T$.

6. The method according to claim 1, wherein a measure is composed for the presence of power matching by determining the power of the 90° pulse at the signal generator and the power of the 90° pulse reflected at the coil, wherein a ratio between the reflected power of the 90° pulse and the power of the 90° pulse at the signal generator is determined.

7. A method for determining a pulse duration $T_{90}$ of a 90° pulse in a nuclear magnetic measuring method with a circuit arrangement that has a signal generator for generating the 90° pulse that has a known generator resistance $R_S$, a coil for transmitting the 90° pulse to a medium that has a coil impedance $Z_L$ with a coil resistance $R_L$ and a coil reactance $X_L$ according to $Z_L=R_L+jX_L$, a coupling circuit has a matching capacitor having an adjustable matching capacitance $C_M$ and a tuning capacitor (13) having an adjustable tuning capacitance $C_T$, and an angular resonance frequency $\omega_0$, the method comprising:

magnetizing the medium by a magnetic field that has a Larmor precession having an angular Larmor frequency $\omega_P$, setting the matching capacitance $C_M$ and the tuning capacitance $C_T$ of the coupling circuit so that the angular resonance frequency $\omega_0$ corresponds to the angular Larmor frequency $\omega_P$ and power matching is present between the signal generator and the coil, in circuit arrangement, determining the coil resistance $R_L$, in circuit arrangement after the setting of the matching and tuning capacitances determining the pulse duration $T_{90}$ of the 90° pulse in the nuclear magnetic measuring method as a function of the coil resistance $R_L$, which is then output as the pulse duration determined, wherein the function of the coil resistance $R_L$ is $$R_L = A + BT_{90} - CT_{90}^3 + \frac{DT_{90}}{E + T_{90}^2}$$

wherein A, B, C, D and E are stored constants, and wherein the constants A, B, C, D and E are determined from a system of equations, wherein the system of equations is formed by the resistance $R_L$ being determined for at least five different pulse durations $T_{90}$ of the 90° pulse and the respective resistance $R_L$, and by the respective pulse duration $T_{90}$ being applied to the equation $$R_L = A + BT_{90} - CT_{90}^3 + \frac{DT_{90}}{E + T_{90}^2}.$$

8. The method according to claim 1, wherein at least one of the matching capacitance $C_M$ and the tuning capacitance $C_T$ is scaled in that a quotient formed of the angular resonance frequency $\omega_0$ as dividend and a reference angular resonance frequency $\omega_0^n$ as divisor is multiplied by at least one of the matching capacitance $C_M$ and the tuning capacitance $C_T$.

9. The method according to claim 8, wherein the magnetic field is generated using permanent magnets and the reference angular resonance frequency $\omega_0^n$ is determined at a temperature of the permanent magnets.

10. A nuclear magnetic flowmeter for a nuclear magnetic measuring method, comprising:

a circuit arrangement having a signal generator for generating a 90° pulse, a coil for transmitting the 90° pulse to a medium, a coupling circuit and an angular resonance frequency $\omega_0$, and a control unit wherein the signal generator has a known generator resistance Rs, wherein the coil has a coiled impedance $Z_L$ with a coil resistance $R_L$ and a coil reactance $X_L$ according to the relationship $Z_L=R_L+jX_L$, the coupling circuit has a matching capacitor having an adjustable matching capacitance $C_M$ and a tuning capacitor having an adjustable tuning capacitance $C_T$, and wherein the flowmeter is configured to magnetize the medium by a magnetic field so that the medium has a Larmor precession with an angular Larmor frequency $\omega_P$, wherein the control unit is configured for determining a pulse duration $T_{90}$ of a 90° pulse, wherein the control unit is configured for setting the matching capacitance $C_M$ and the tuning capacitance $C_T$ of the coupling circuit, such that an angular resonance frequency $\omega_0$, corresponds to the angular Larmor frequency $\omega_P$, and power matching is present between the signal generator and the coil, wherein the control unit is configured for determining the coil resistance $R_L$, in circuit arrangement after the setting of the matching and tuning capacitances wherein the control unit is configured for determining the pulse duration $T_{90}$ of the 90° pulse in the nuclear magnetic measuring method as a function of the coil resistance $R_L$, and outputting the pulse duration determined.

11. The nuclear magnetic flowmeter according to claim 10, wherein the coil resistance $R_L$ is determined by using the generator resistance $R_S$, the angular resonance frequency $\omega_0$, the matching capacitance $C_M$ and the tuning capacitance $C_T$.

12. The nuclear magnetic flowmeter according to claim 10, wherein the coil reactance $X_L$ is assumed to be constant and the coil resistance $R_L$ is determined by using the generator resistance $R_S$, the angular resonance frequency $\omega_0$, and either the matching capacitance $C_M$ or the tuning capacitance $C_T$.

13. The nuclear magnetic flowmeter according to claim 12, wherein the coil reactance $X_L$ assumed to be constant is determined by using the generator resistance $R_S$, the angular resonance frequency $\omega_0$, the matching capacitance $C_M$ and the tuning capacitance $C_T$.

14. The nuclear magnetic flowmeter according to claim 10, wherein the magnetic field is generated by using permanent magnets.

* * * * *